（12）United States Patent
La Forgia et al.

(10) Patent No.: US 7,543,565 B2
(45) Date of Patent: Jun. 9, 2009

(54) OPTICAL SYSTEM FOR DETECTING THE CONCENTRATION OF COMBUSTION PRODUCTS

(75) Inventors: Domenico La Forgia, Bari (IT); Arturo Antonio De Risi, Lecce (IT); Massimo De Vittorio, Lecce (IT); Roberto Cingolani, Lecce (IT); Adriana Passaseo, Lecce (IT); Mauro Lomascolo, Lecce (IT)

(73) Assignee: Consiglio Nazionale Delle Ricerche - INFM, Genova (IT)

( * ) Notice: Subject to any disclaimer, the term of this patent is extended or adjusted under 35 U.S.C. 154(b) by 394 days.

(21) Appl. No.: 10/584,026

(22) PCT Filed: Dec. 22, 2004

(86) PCT No.: PCT/IB2004/004253

§ 371 (c)(1),
(2), (4) Date: Jun. 21, 2006

(87) PCT Pub. No.: WO2005/064315

PCT Pub. Date: Jul. 14, 2005

(65) Prior Publication Data

US 2007/0152237 A1    Jul. 5, 2007

(30) Foreign Application Priority Data

Dec. 22, 2003   (IT)   ............... BA2003A000066

(51) Int. Cl.
*H01L 31/0264*   (2006.01)
*H01L 31/0352*   (2006.01)
*G01N 21/33*   (2006.01)

(52) U.S. Cl. .................... 123/435; 257/184

(58) Field of Classification Search ............ 123/703, 123/672; 257/21, 184
See application file for complete search history.

(56) References Cited

U.S. PATENT DOCUMENTS 4,614,961 A    9/1986   Khan et al.

(Continued)

OTHER PUBLICATIONS

Morkoc, H., "Potential applications of III-V nitride semiconductors", Materials Science and Engineering, vol. 43, No. 1-3, pp. 137-146 (1994).

(Continued)

*Primary Examiner*—Stephen K Cronin
*Assistant Examiner*—Arnold Castro
(74) *Attorney, Agent, or Firm*—Venable LLP; Michael A. Sartori; Catherine M. Voorhees

(57) ABSTRACT

Optical system for detecting the concentration of combustion products operating in situ and at high temperature based on measurement of the optical absorption of a gaseous mixture of combustion products through a photodetecting sensor based on gallium nitride (GaN), aluminium nitride (AlN), indium nitride (InN) and corresponding alloys. The operating temperature of the sensor preferably lies between 500° C. and 700° C., but the resistance of the active material permits use at even higher temperatures. This system can be used to measure the concentration of chemical species present in combustion products directly at their outlet, where the high operating temperature makes it possible to avoid fouling of the sensor caused by carbonaceous and non-carbonaceous deposits. The rate of response of the system is less than or equal to 1 millisecond and makes it possible to adjust the parameters of an associated combustion process control system in real time.

13 Claims, 3 Drawing Sheets

U.S. PATENT DOCUMENTS

Figure 1:
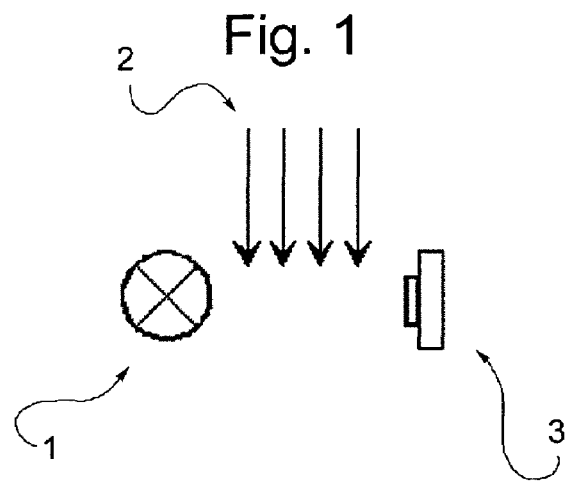

| | | | |
|---|---|---|---|
| 4,796,590 | A | 1/1989 | Degobert et al. |
| 5,182,670 | A * | 1/1993 | Khan et al. .................... 257/21 |
| 5,278,435 | A * | 1/1994 | Van Hove et al. ........... 257/184 |
| 5,979,423 | A * | 11/1999 | Poindexter et al. .......... 123/703 |
| 7,119,359 | B2 * | 10/2006 | Alfano et al. ................. 257/21 |

OTHER PUBLICATIONS

Morkoc, H., et al., "GaN-based modulation doped FETs and UV detectors", Solid-State Electronics, vol. 46, No. 2, pp. 157-202 (Feb. 2002).

POTI, et al., "High responsivity GaN-based UV detectors", Electronics Letters, vol. 39, No. 24, pp. 1747-1749 (Nov. 27, 2003).

Henini, M., "III-V nitrides for electronic and UV applications", III Vs Review, vol. 12, No. 5, pp. 28, 30-32 (Sep. 1999).

Strite, S., et al., "Progress and prospects for GaN and the III-V nitride semiconductors", Thin Solid Films, vol. 231, No. 1/2, pp. 197-210 (Aug. 25, 1993).

Strite, S., et al., "GaN, AlN, and InN: A Review", Journal of Vacuum Science and Technology, vol. 10, No. 4, pp. 1237-1266 (Jul. 1992).

Scherer, A., et al., "InGaAsP photonic band gap crystal membrane microresonators", Journal Of Vacuum Science & Technology, vol. 16, No. 6, pp. 3906-3910 (Nov. 1998).

Monroy, E., et al, "AlGaN-based UV photodetectors", Journal of Crystal Growth, vol. 230, No. 3-4, pp. 537-543 (Sep. 2001).

De Vittorio, M., et al., "High temperature characterization of GaN-based photodetectors", Sensors and Actuators, vol. 113, No. 3, pp. 329-333 (Jun. 9, 2004).

* cited by examiner

WAVE GUIDE

OPTICAL SYSTEM FOR DETECTING THE CONCENTRATION OF COMBUSTION PRODUCTS

This invention relates to a system for detecting the concentration of gaseous species, and more specifically combustion products.

Such a system finds application in the automotive industry, in the analysis of gases in fixed and laboratory equipment and in environmental monitoring (for example units for detecting the quality of urban air and similar equipment).

On-line control of combustion processes in an internal combustion engine (diesel or petrol) is a requirement which is very much felt in the automotive industry. The possibility of feedback control and adjusting combustion process parameters in real time allows full optimisation, even under transitional conditions. Both fuel consumption and residual polluting emissions are as a consequence reduced, and it is also possible to compensate for any losses of performance from components due to wear.

At the present time residual emissions are monitored in the laboratory/workshop, where there are bench instruments which use sensors based on chemiluminescence for the detection of $NO_x$ gases (mainly NO and $NO_2$) and infrared absorption sensors for hydrocarbons HC and carbon oxides CO, $CO_2$. The only sensor with which motor vehicles are fitted is the lambda sensor which can be used for the on-line monitoring of oxygen $O_2$ only.

Photodetection technology for measuring the concentration of gas species has already been successfully applied in the infrared spectral region and is based on materials such as silicon, germanium and gallium and indium arsenides. However, these materials are unsuitable for, and have little resistance to high temperatures, which degrade their performance and drastically reduce their service lives.

Gallium nitride and its compounds on the other hand are highly resistant materials which are particularly suitable for work in aggressive environments. In addition to this the energy gap, which is greater than 3 eV even at high temperatures, renders them insensitive to visible radiation, and suitable for the manufacture of electronic devices operating in the ultraviolet spectral region and at temperatures even above 500° C., bringing about an improvement in the signal/noise ratio.

The international patent literature describes gallium-nitride-based sensors for determining the concentration of chemical species; these sensors comprise a transistor in which the conductivity of the channel varies according to adsorption of the gaseous species in question and is therefore based on a different principle of operation. As a consequence these have response times of a different order of magnitude which are longer than those required for use in the on-line control of combustion processes. For example, a sensor using gallium nitride and its components having a transistor structure used for the detection of $H_2$, $O_2$, HC and CO produced by combustion in a motor vehicle internal combustion engine is claimed in German Patent DE 10032062. The gases are detected by monitoring the electrical characteristics of the transistor brought about through the adsorption of these chemical species onto the active surface of the sensor. Given that this principle of measurement is different from the optical principle, its response times are of the order of one second.

The main disadvantage of known technologies lies in the fact that the construction of an immediate and in situ monitoring system for residual emissions of $NO_x$, CO, $CO_2$ and HC gases is impeded by the slow response time, of the order of seconds, of sensors based on the adsorption of these gaseous species by the active material. Conversely, existing optical sensors cannot be used at high temperatures, thus making it inevitable that they are positioned in the exhaust ducts for combustion products, with the sensor becoming fouled because of the deposition of carbonaceous and not carbonaceous residues, on the sensitive surface. Detection which is not in situ and the long response times do not permit real-time monitoring of the parameters controlling the combustion process.

The object of this invention is to provide a system for detecting the concentration of combustion products which overcomes the disadvantages of the known art, is resistant to high temperatures and permits real-time monitoring of the parameters in a combustion process.

With this aim the object of this invention comprises an optical system for detecting the concentration of gaseous species, and combustion products in particular, operating in situ and at high temperature, having the characteristics specified in claim 1.

In brief, the system is based on measurement of the optical absorption of a gaseous mixture comprising combustion products using a sensor based on gallium nitride (GaN), aluminium nitride (AlN), indium nitride (InN) and corresponding alloys.

Optical detection of gaseous species brings about an appreciable reduction in the response time of the sensor, now of the order of a millisecond, while the use of gallium nitride and its derivatives makes it possible to produce a selective active material which is resistant to high temperatures and aggressive environments, suitable for work in the ultraviolet spectral region and in its vicinity through the possibility of modulating its energy gap.

In passing through the region between the ultraviolet source and the sensor the gas mixture rich in combustion products varies the emission spectrum of the source—through a combined absorption and emission effect on the part of the gaseous species—and makes it possible to measure the concentrations of the species present.

The main advantages provided by the invention in the automotive field are feedback control and real-time monitoring of combustion parameters and emission reduction systems, even in the case of worn engine or engines which are not functioning in a regular manner and, as a consequence, reduction of polluting agent emissions and the improvement of performance under transitional conditions.

Further features and advantages will be apparent in the course of the detailed description of the invention with specific reference to the appended figures, in which a number of exemplary, non-restrictive preferred embodiments are illustrated.

Figure 2:
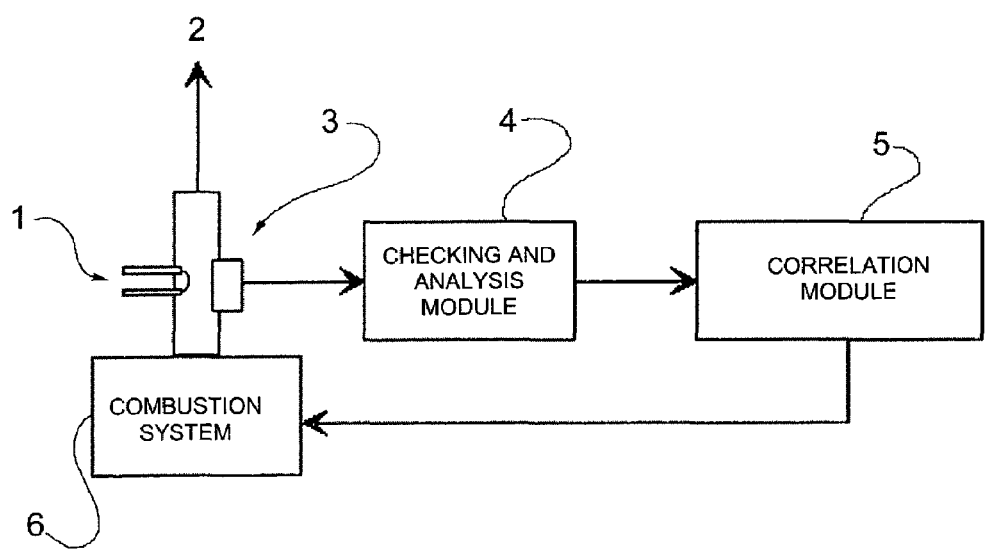
Figure 3A:
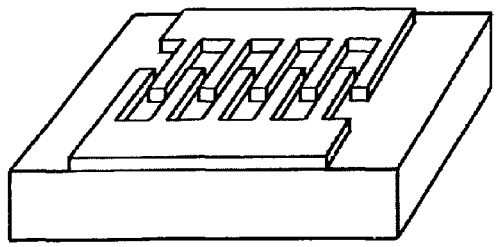
Figure 3B:
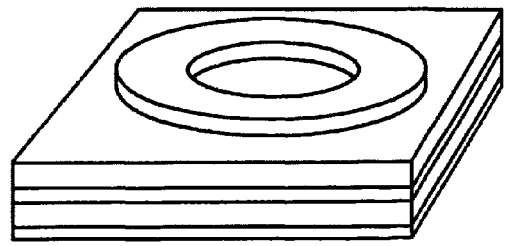
Figure 4A:
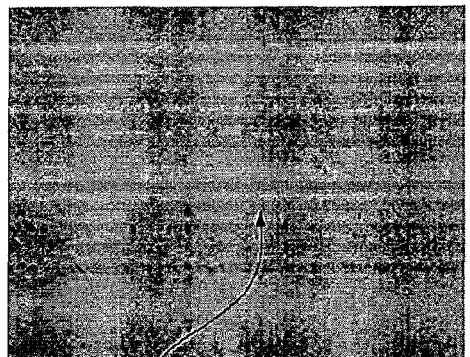
Figure 4B:
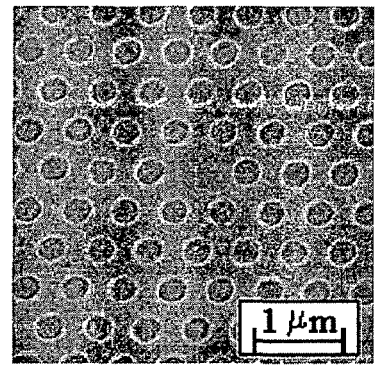
Figure 5:
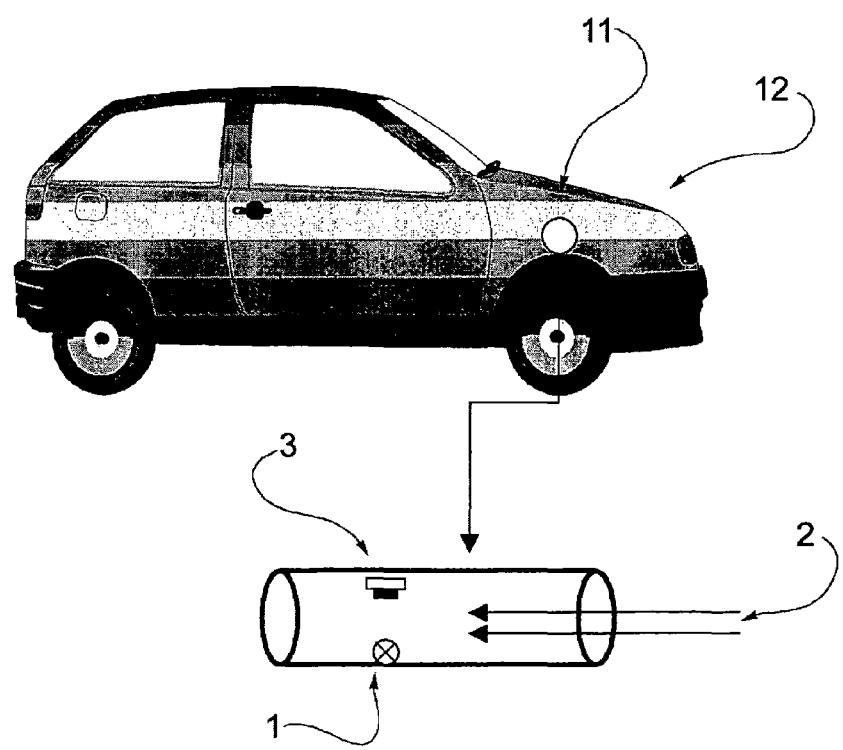
Figure 6:
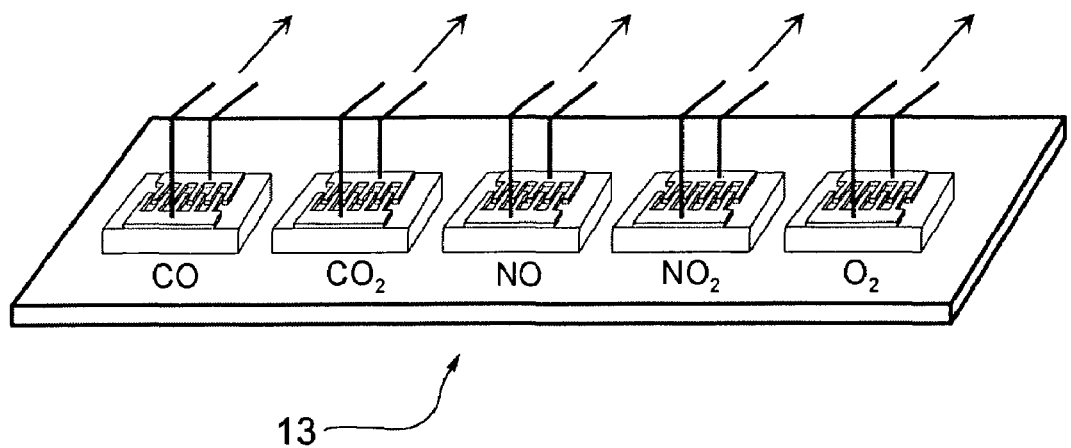
Figure 7:
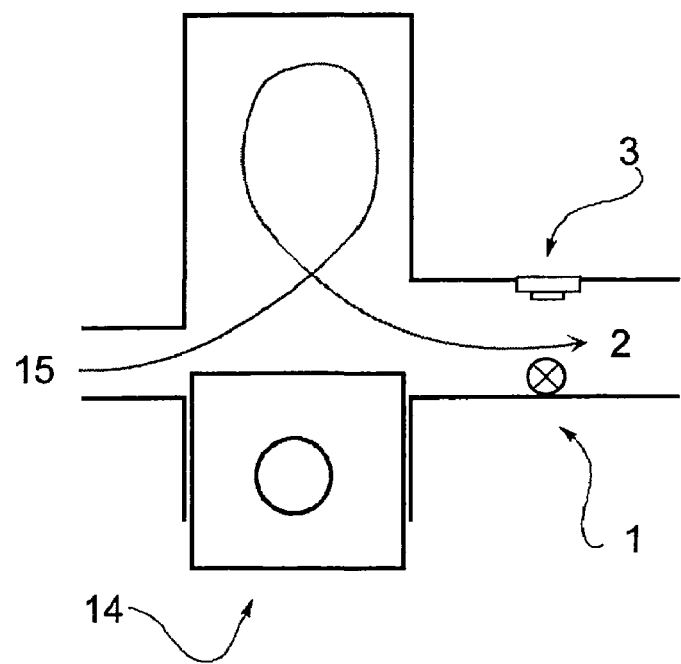

In particular:

FIG. 1 shows a diagram of the optical detection system according to this invention, FIG. 2 shows a diagram of the feedback monitoring of a combustion system based on the optical detection system according to the invention, FIGS. 3a and 3b show two types of structures of the photodetector device according to the invention, FIG. 4 shows two possible structures of a photonic crystal photodetector device according to the invention, FIG. 5 is a diagram of application of the optical detection system to the exhaust system of a motor vehicle internal combustion engine, FIG. 6 shows a photodetector device of the matrix type in relation to the application in FIG. 5, Finally, FIG. 7 is a diagram of application of the optical detection system to a two-stroke compression-ignition engine.

With reference to FIG. 1, the diagram of the system shown comprises an optical source 1 opposite a photodetector device or optical sensor 3. The source operates in the spectral region between blue and ultraviolet and comprises, for example and purely by way of a non-restrictive example, an arc between two electrodes opposite each other within the gas which is to be analysed, which directly illuminates the optical sensor.

The molecules of the gas or gas mixture 2, for example deriving from the combustion process which it is desired to analyse, flow between the electrodes and in the region between the source and the optical sensor, bringing about a change in the spectrum emitted by the arc through a combined absorption and emission effect. From the spectrum detected in optical sensor 3 it is possible to determine the concentrations of the species present in the combustion gases.

The sensor response is preferably used to control the parameters of the combustion system in a closed loop feedback system. The sensor response may be used as in FIG. 2, which is provided purely by way of a non-restrictive example. The output from sensor 3 is first checked in a checking and analysis processing module 4; it is then used as an input to a correlation processing module 5 which provides the concentration of the species investigated. These data are compared with suitable maps to obtain as an output the corrective parameters for operating combustion system 6 in the feedback configuration.

This configuration, which has response times of one millisecond or less, makes it possible to adjust the combustion process control system parameters in real time. The effect of this feedback control on automotive applications makes it possible to effect almost instantaneous monitoring of the parameters controlling combustion (injection pressure, throughflow, advance and duration of injection, number of injections, etc.) and the emission reduction systems (quantity of catalyst, regeneration strategies, etc.), the possibility of altering engine control parameters in an optimum way even in worn systems or systems not functioning in a regular manner, the reduction of polluting agent emissions, and the improvement of performance under transitional conditions.

Other fields of application are gas analysers for both fixed equipment and laboratory equipment.

Optical sensor 3 is the heart of the detection system. This comprises gallium nitride (GaN), aluminium nitride (AlN) or indium nitride (InN) and corresponding alloys as the active material and is produced on a substrate of sapphire ($Al_2O_3$) or silicon carbide (SiC) or silicon using the epitaxial growth technique. The mechanical and physical properties of the constituent material allow it to be used at very high temperatures and make it compatible with particularly aggressive environments such as those present in combustion gas exhaust ducts where high temperatures and pressures, dust, acid environments, etc., are simultaneously present. In addition to this the energy gap of the compounds based on gallium nitride, over 3 eV at high temperature, renders it transparent to visible and infrared radiation, improving the signal to noise ratio when detecting signals in the ultraviolet. This characteristic is made use of in this invention for the production of optical sensors operating in the UV spectral region.

Spectral discrimination of the various absorption lines and therefore the gases may be effected in different ways and in particular by:
  varying the active material to selectively increase or reduce absorption in specific spectral regions having wavelengths between 200 nm and 500 nm (the absorption of nitride-based compounds may be varied continuously between 200 nm and 500 nm by forming alloys between AlN and GaN or between GaN and InN),
  electronic engineering of the band structure of the device, i.e. by alternating thin layers of different materials in such a way as to form quantum wells,
  photonic engineering of the band structure, that is permitting only specific photon transitions through the construction of photonic crystal optical microresonators.

In the first case the possibility of producing gallium nitride (GaN), aluminium nitride (AlN) or indium nitride (InN) and corresponding alloy heterostructures through epitaxial deposition with precise control of the number of lattice planes and the composition of the compound makes it possible to construct quantum confinement nanostructures where the absorption band can be reduced to a few tens of Å tuned at will in the region of the ultraviolet through control of the thickness and composition of the alloy having the lowest energy gap (for example GaN) lying between two high energy gap barriers (for example AlGaN).

In addition to this, the deposition of AlGaN alloys having a different aluminium content makes it possible to shift the energy of the energy gap from blue to deep UV, while the deposition of InGaN alloys having different indium contents makes it possible to reduce the energy of the energy gap and therefore extension of the spectral absorption band to the visible (green and yellow).

For example, for the detection of NO, one of the most intense spectral lines of which is at a wavelength of 338.64 nm, the optical sensor is constructed using a material which is photosensitive with a spectral band comprising that wavelength and/or through inserting such a material in a structure which eliminates all the spectral components except that at 338.64 nm (microcavities, multilayer filters, etc.).

Possible constituent structures of the optical sensor are listed below:
  GaN (massive gallium nitride), for the detection of spectral lines having a wavelength of 360 nm or higher,
  $Al_xGa_{1-x}N$ (gallium aluminium nitride), $0 \leq x \leq 1$; for detecting spectral lines having a wavelength of 206 nm or higher; as x is varied the value of the wavelength varies between 206 nm and 360 nm,
  $In_xGa_{1-x}N$ (gallium indium nitride), $0 \leq x \leq 1$; for the detection of spectral lines having a wavelength of 360 nm or higher; as x varies the value of the wavelength varies between 360 nm and 500 nm,
  multi-quantum wells of GaN/AlGaN, InGaN/GaN.

Examples of embodiments of the sensor provided by way of a non-restrictive example are provided below.

EXAMPLE 1

Construction of the Sensor With a Massive GaN Structure.

The photosensitive material is synthesised through vapour phase epitaxial growth. Prior to growth the sapphire (or SiC or Si) substrate is subjected to heat treatment at a temperature of 1100° C. in a flow of hydrogen ($H_2$) at a pressure of 20 mbar for a minimum time of 15 minutes. Subsequently the reactor temperature is reduced to 560° C. and the pressure increased to 450 mbar for growth of the nucleation layer of GaN with a thickness of between 20 nm and 200 nm, which is performed in a $N_2$ environment, feeding controlled flows of the growth precursors (gaseous ammonia ($NH_3$) and trimethylgallium (TMGa)) to the reactor. The composition (GaN or AlN or AlGaN), the growth conditions (temperature and pressure)

and the thickness of the nucleation layer may vary depending upon the substrate used. The nucleation layer is subjected to further thermal annealing treatment which is carried out at a temperature of 1100° C. in a $N_2$ and $NH_3$ environment. Subsequently the GaN (photosensitive material) is deposited at a temperature of 1150° C. and a pressure of 50 mbar in a $H_2$ environment with a deposition rate of 2 μm/h, feeding controlled flows of $NH_3$ and TMGa.

Interdigitating contacts are then produced on the epitaxial structure through standard photolithographic processes and metal (for example aluminium) contacts deposition by thermal evaporation and/or by electron beam.

EXAMPLE 2

Production of a Sensor Having a Massive AlGaN Structure

Production is carried out as in Example 1 with the only difference that for preparation of the photosensitive material (AlGaN) a flow of trimethylaluminium (TMAl) is added to the feed flows and the growth temperature could be raised up to 1180° C.

EXAMPLE 3

Production of a Sensor Having a Massive InGaN Structure

Production is carried out as in Example 1 with the only difference that for preparation of the photosensitive material (InGaN) a flow of trimethylindium (TMIn) is added to the feed flows, the growth temperature could be reduced (to 720° C.) and growth could take place in a nitrogen environment.

EXAMPLE 4

Production of a Sensor With a Multi-Quantum Well Structure.

Production is carried out as in Example 1 with the only difference that the following sequence is used for preparation of the photosensitive material:
1. Growth of a buffer layer of GaN as in Example 1 with a minimum thickness of 1 μm,
2. Growth of a AlGaN barrier as in Example 2 with a minimum thickness of 10 nm,
3. Growth of a quantum well of GaN as in Example 1, with a thickness depending on the spectral line requiring detection and the Al content of the barrier. For example, in order to detect the line of NO at 338.64 nm the thickness of the quantum well would be 1.9 nm for an AlGaN barrier aluminium content of 18%,
4. Repetition of stages 2 and 3 through a number of times equal to the number of quantum wells required in order to obtain the desired degree of responsiveness from the optical sensor.

The sequence illustrated is used to grow quantum wells comprising layers of GaN/Al(Ga)N. In the case of quantum wells of In(Ga)N/GaN, step 3 comprises growing InGaN as in Example 3.

In the case of multi-quantum well structures precise control of the thickness and composition of the layers makes it possible to vary the absorption band, making it possible to discriminate the absorption lines of various gases. Every type of heterostructure can therefore be used to detect one or more gaseous species.

Two possible types of optical sensor, having the heterostructures just described as photosensitive material, are illustrated in FIGS. 3a and 3b.

FIG. 3a shows a structure with interdigitated co-planar metal-semiconductor-metal contacts. The photogenerated electric current is detected through the application of a voltage across the two interdigitated contacts. In this case the active material is close to the surface of the sample.

FIG. 3b instead shows a type of optical sensor having a p-i-n structure. In this case transport is vertical between two contacts located on the surface and the substrate respectively.

In both cases light falls upon the device and is absorbed within the active material generating electron-hole pairs which are collected in the form of electrical current through two metal contacts deposited on the device.

Through photonic engineering of the band structure it is instead possible to use an active material with a wide spectral response band from which a small spectral region is subsequently selected.

To this aim the photosensitive material is inserted into photonic crystal microcavity devices in order to modify the density of the photonic states in the device and permit optical absorption transitions only at the wavelengths of interest. The permitted photonic modes are selected through photonic crystal technology which makes it possible to control the permitted electromagnetic modes in a medium having a periodic refractive index. Suitable selection of the periodicity (of the order of a fraction of a wavelength) in particular directions in a photonic crystal brings about constructive interference of the required wavelength through multiple reflections, and this is caused to coincide with the absorption/emission line for the gas being analysed.

Two possible structures for the photonic crystal device are illustrated in FIGS. 4a and 4b.

FIG. 4a shows an electron microscope image of a vertical cavity device for the selection of a single atomic absorption line. This device has the advantage that it can be produced directly during the stage of epitaxial growth. In this case the resonator comprises the central region of the device, indicated as a waveguide and containing the absorbent material inserted between two Bragg type reflectors. All the light falling on the resonator is reflected because of the multiple reflections at the interfaces, with the exception of a narrow permitted wavelength band (called the resonance frequency of the cavity) in the waveguide which depends on its thickness and the refractive index of the photosensitive material.

These multilayer structures produce single dimension photonic crystals (structures in which the periodicity of the refractive index lies along a single dimension). The thickness and refractive index of the waveguide determine the number and spectral position of the permitted longitudinal modes in the device.

For example, in the case of the spectral line at 338.64 nm which identifies the gas NO, the structure described is constructed through vapour phase epitaxial growth as previously described in Example 1, with the only difference that the following sequence was used to produce the photosensitive material:
1. growth of a buffer layer of GaN as in Example 1, with a minimum thickness of 1 μm,
2. growth of a layer having a lower refractive index (AlN) as in Example 2, having a thickness equal to $\lambda/4n_{AlN}$, where $\lambda$ is the design wavelength (338.64 nm) and $n_{AlN}$ is the refractive index of AlN at 338.64 nm, which is equal to approximately 2.09. In the case in question the thickness was then equal to 40.5 nm, 3. growth of a layer having a greater refractive index (GaN) as in Example 2 having a thickness equal to $\lambda/4n_{GaN}$, where $\lambda$ is the design wavelength (338.64 nm) and $n_{GaN}$ is the refractive index of GaN at 338.64 nm, which is equal to approximately 2.53. In the case in question the thickness was then equal to 33.5 nm,
4. repetition of steps 2 and 3 for the required number of pairs of layers having different refractive indices,
5. growth of the resonant cavity (GaN) having a thickness of $\lambda/n_{GaN}$, or a whole multiple of $\lambda/2n_{GaN}$, where $\lambda$ is the design wavelength (338.64 nm) and $n_{GaN}$ is the refractive index of GaN at 338.64 nm, which is equal to approximately 2.53. In the case in question the thickness $\lambda/n_{GaN}$ was therefore equal to 133.8 nm,
6. repetition of stages 2 and 3 for the necessary number of periods.

FIG. 4b shows an electron microscope image of another example of a structure of the optical sensor based on two-dimensional photonic crystals.

In this case periodicity of the refractive index is produced in the plane of the photosensitive material through high resolution technological processes subsequent to the epitaxial growth (in the example in the figure periodical air holes are produced in the photosensitive material). The incorporation of a "defect" into the photonic crystal, such as for example the absence of a hole as in the figure, forms a microcavity whose optical properties, that is the permitted wavelengths, are determined by the geometrical parameters of the structure. The advantage of this structure is therefore that of being able to produce devices which are sensitive to radiation of different wavelength on the same substrate merely by varying the periodicity and diameter of the photonic crystal and the nature of the "defect".

In this case the sensor is produced using structures as described in Examples 1, 2, 3 and 4 (excluding the deposition of electrodes) on which the following technological steps are performed:
1. deposition of a resist (for example PMMA),
2. creation of the photonic crystal pattern through direct writing by lithography using a high resolution electron beam and/or optical lithography,
3. transfer of the pattern to produce a matrix of holes in the material (or columns) having a periodicity and diameter dependent on the spectral line which has to be detected, through selective physical/chemical etching (RIE).

The optical selection function can also be achieved through depositing dielectric multilayers subsequent to epitaxial growth of the active material. The alternation of transparent layers having a different refractive index (e.g. $TiO_2$ to $SiO_2$) makes it possible to achieve pass-band or notch functions, that is the transmission or attenuation of a narrow spectral band, selecting the wavelengths which can be transmitted or attenuated through the use of multiple reflections. The use of $TiO_2$ in the presence of UV radiation also has the advantage of catalysing the degradation of organic materials which are not oxidised at the sensor's high operating temperatures, preventing fouling.

A combination of the preceding two technologies (simultaneous engineering of the electronic band and photonic structures) makes it possible to detect very narrow transitions even at high temperatures. One example of the combination of the two techniques may be the insertion of quantum wells in an optical microcavity operating at the same wavelength (spectral line of the gas of interest).

Finally, it should be pointed out that in another embodiment of the detector optical system the photodetector device may comprise a matrix of optical sensors connected together so that they can be controlled independently and operate at different spectral frequencies. For example the sensor array may comprise 5 independent elements comprising structures prepared as in Example 4 in which the thicknesses and/or compositions of the layers of quantum wells have been designed to detect a single spectral line identifying CO in element 1, $CO_2$ in element 2, NO in element 3, $NO_2$ in element 4 and $O_2$ in element 5 (see FIG. 6). As an alternative the individual elements in the array may comprise structures constructed as in Example 5 in which the thicknesses of the reflecting layers and the resonant cavity have been designed to detect a single spectral line identifying the gas which has to be detected.

In both cases the signal originating from the individual sensors is compared with a reference signal and used in the feedback system to correct the combustion parameters in real time as described in the examples provided below in relation to a number of fields of application in the automotive industry.

Example of Application in the Automotive Field

The optical detection system is mounted on the exhaust ducts upstream from the supercharger system (where present) and in any event as close as possible to the propulsion system's exhaust. Diagrammatically, this device is fitted in the position indicated by a white circle (11) in FIG. 5 superimposed on the image of a motor vehicle (12), and a possible layout of the emitter-sensor system is shown in the enlarged view.

The photodetector device is of the matrix type and comprises an array of individual optical sensors each of which is capable of detecting a single wavelength (or a narrow spectral band) unequivocally identifying a particular gaseous species present in the exhaust gas. Purely by way of example and without limitation a matrix (13) of 5 devices, illustrated in FIG. 6, may be used, each of these detecting the concentration of one of the following 5 gases, CO, $CO_2$, NO, $NO_2$, $O_2$, independently of the others. The devices are constructed as described in the examples, using one or more of the spectral selection techniques already described.

An arc lamp positioned opposite the sensitive area of the sensors locally excites the gas flowing between the sensor and the lamp causing the emission of spectral lines which identify the gaseous species present.

The array of sensors detects the intensities of the specific spectral lines through an electrical signal. The output signal from each of the devices is typically a photogenerated current having an intensity which is proportional to the concentration of the species for which the individual sensor has been designed.

The signal is filtered and conditioned so that it can be used as an input to the feedback control system (FIG. 2) to control the process parameters, that is for example the number of injections and the manner in which the fuel is injected.

Example of Application in Two-stroke Injection Engines

With reference to the diagram in FIG. 7, it will be seen that, unlike the case of four-stroke engines, because of the direct connection between inlet duct 15 and exhaust duct 2 during the washing stage, in two-stroke engines the measured airflow entering the engine is not the same as the quantity of air which is actually available for combustion.

The sensor is designed to be sensitive to the oxygen concentration and is constructed in accordance with one of the previous examples of construction.

The sensor is in thermal contact with a heater (e.g. a resistance heater) which has the function of rapidly raising the temperature of the device (to a few hundred degrees centigrade) and keeping it there in order to encourage the decomposition of unburnt residues and thus avoid the deposition of carbonaceous and non-carbonaceous residues.

An output electrical signal from the sensor makes it possible to determine the oxygen content of the combustion gases in real time and therefore to make an accurate calculation of the quantity of air trapped within the cylinder.

The signal is filtered and processed in such a way that it can be used as an input to the feedback control system (FIG. 2) to control the injection parameters.

This cannot be carried out with known sensors because these are unable to measure the oxygen content with sufficiently fast response times for such an application.

Of course the embodiments and details of construction may be varied widely from what has been described and illustrated purely by way of a non-restrictive example without thereby going beyond the scope of protection of this invention as defined by the appended claims.

The invention claimed is:

1. A system for controlling a combustion process in a motor vehicle internal combustion engine, characterized by an optical system for detecting the concentration of gaseous species, mounted on an exhaust duct of the engine, and comprising at least one source of ultraviolet and/or visible radiation and a photodetector device opposite that source, between which there flows an exhaust gaseous mixture, wherein the said radiation source is adapted to locally excite the gaseous mixture so as to bring about a combined absorption and emission effect by the exhaust gaseous species present, and wherein the said photodetector device comprises an active material based on gallium nitride (GaN), aluminium nitride (AlN) or indium nitride (InN) and corresponding alloys and is adapted to determine the concentration of the gaseous species present in the mixture through detection of the change in the spectrum emitted by the source.

2. A system according to claim 1, in which the said system for detecting the concentration of gaseous species includes heating means adapted to stabilize and maintain a predetermined operating temperature in the photodetector device to encourage the decomposition of unburnt residues and prevent the deposition of carbonaceous and non-carbonaceous residues.

3. A system according to claim 1, characterized in that spectral discrimination of the different absorption lines is effected by engineering the electronic band structure of the photodetector device, that is by alternating layers of different materials so as to form quantum wells.

4. A system according to claim 1, characterized in that spectral discrimination of the different absorption lines is effected by engineering the photonic band structure of the photodetector device, that is by permitting only specific photon transitions through constructing photonic crystal optical microresonators.

5. A system according to claim 1, characterized in that the active material comprised in the photodetector device is massive gallium nitride adapted to detect spectral lines having a wavelength of 360 nm or higher.

6. A system according claim 1, characterized in that the active material comprised in the photodetector device is gallium aluminium nitride ($Al_xGa_{1-x}N$ with $0 \leq x \leq 1$) adapted to detect spectral lines having a wavelength varying between 206 nm and 360 nm as x vanes.

7. A system according to claim 1, characterized in that the active material comprised in the photodetector device is gallium indium nitride ($In_xGa_{1-x}N$, with $0 \leq x \leq 1$) adapted to detect spectral lines having a wavelength varying between 360 nm and 500 nm as x vanes.

8. A system according to claim 1, characterized in that the active material comprised in the photodetector device includes quantum wells of GaN/AlGaN or InGaN/GaN.

9. A system according to any of claims 5 to 8, characterized in that the said active material is inserted into a device which has co-planar metal-semiconductor-metal contacts.

10. A system according to any of claims 5 to 8, characterized in that the said active material has a heterostructure with a p-i-n structure.

11. A system according to any of claims 5 to 8, characterized in that spectral discrimination of the different absorption lines is effected by engineering the photonic band structure of the photodetector device, that is by permitting only specific photon transitions through constructing photonic crystal optical microresonators and in that the photonic crystal microresonator device has a vertical cavity structure for the selection of a single atomic absorption line produced during a stage of epitaxial growth including a central waveguide region containing the absorbent material inserted between two Bragg-type reflectors.

12. A system according to any of claims 5 to 8, characterized in that the photodetector device has a structure based on two-dimensional photonic crystals.

13. A system according to claims 1 to 4, characterized in that it comprises a matrix of photodetector devices which can be controlled independently and which comprise different active materials among gallium nitride (GaN), aluminium nitride (AiN), indium nitride (InN) and corresponding alloys, adapted to operate at respectively different spectral frequencies.

* * * * *